United States Patent [19]

Fujikawa et al.

[11] Patent Number: 4,983,524

[45] Date of Patent: Jan. 8, 1991

[54] METHOD OF IMMOBILIZING ENZYMES ON A SUPPORT WITH IRIDOID A GLYCONE CROSS-LINKING AGENTS

[75] Inventors: Shigeaki Fujikawa; Kunimasa Koga; Tomoko Yokota, all of Osaka, Japan

[73] Assignee: Suntory Limited, Osaka, Japan

[21] Appl. No.: 135,354

[22] Filed: Dec. 21, 1987

[30] Foreign Application Priority Data

Dec. 19, 1986 [JP] Japan .................................. 61-302966

[51] Int. Cl.$^5$ ...................... C12N 11/00; C12N 11/10; C12N 11/08; C12N 11/06
[52] U.S. Cl. .................................... 435/174; 435/176; 435/177; 435/178; 435/180; 435/181; 435/182
[58] Field of Search ................ 435/174, 176, 177, 178, 435/180, 181, 182; 546/112

[56] References Cited

U.S. PATENT DOCUMENTS

| | | | |
|---|---|---|---|
| 3,796,634 | 3/1974 | Haynes et al. ................... | 435/176 X |
| 3,873,426 | 3/1975 | Katchalski et al. ................ | 435/176 |
| 4,247,698 | 1/1981 | Toyama et al. ..................... | 546/112 |
| 4,347,356 | 8/1982 | Touyama et al. ................... | 546/112 |

OTHER PUBLICATIONS

Biotechnol. Bioeng. Symp., 12, 485 (1982).
Biotechnol. Bioeng. Symp. 25, 2411 (1983).
J. Biochem., 62, 419 (1967).
Zaborsky, O. R., Biomedical Applications of Immobilized Enzymes and Proteins, vol. 1, 1977, (pp. 25–35).

*Primary Examiner*—David M. Naff
*Attorney, Agent, or Firm*—Cushman, Darby & Cushman

[57] ABSTRACT

An enzyme is immobilized by contacting the enzyme with a support in a solution containing an iridoid aglycone cross-linking agent. The cross-linking agent may be genipin or an aglycone or an iridoid glycoside such as geniposide, gardenoside or geniposide acid.

10 Claims, 4 Drawing Sheets

METHOD OF IMMOBILIZING ENZYMES ON A SUPPORT WITH IRIDOID AGLYCONE CROSS-LINKING AGENTS

FIELD OF THE INVENTION

The present invention relates to a method of immobilizing an enzyme using a cross-linking agent selected from iridoids to facilitate immobilization of the enzyme on a substrate. More specifically, the present invention relates to a method for producing an immobilized enzyme which is equally as active as the free enzyme, is stable and nontoxic, and is hence particularly suitable for the production of food material. In order to produce such an immobilized enzyme, the invention utilizes an iridoid which facilitates the polymerization of an enzyme through intermolecular cross-linking and/or helps to form the cross-linkage between the enzyme and the support or substrate.

PRIOR ART

Enzymes from microorganisms, plants or animals are commonly used in biochemical reactions in a variety of fields including the food and pharmaceutical industries. Attempts have also been made to immobilize enzymes on an appropriate support so as to enable the recycled use of said enzymes on a commercial scale instead of using them in batch processes. Immobilized enzymes have been employed in the food industry due to their high efficiency. However, a method of immobilizing enzymes which is accompanied by a high degree of safety, high enzyme activity, high stability and the potential for wide-ranging applications still needs to be developed.

"Support-binding methods", "cross-linking-polymerizing methods", "gel-inclusion methods" and "combination methods" (i.e. a combination of a support-binding method or a cross-linking-polymerizing method with a "gel-inclusion method" have been known.

Gel-inclusion methods are most suitable for the production of food materials from the viewpoint that enzymes are enclosed in polymer matrix or micro-capsules which permit the least amount of denaturation of enzymes and/or avoidance of the need to use a toxic cross-linking agent. However, enzymes are not bound by cross-linkage in this method so the leaking out or loss of enzymes is a serious problem which remains to be solved.

In cross-linking methods, a bifunctional agent such as glutaraldehyde is reacted with an enzyme to effect the cross-linking polymerization and immobilization of the enzyme on a support. Even though this method can avoid the problem of the enzyme leaking out, it is not suitable for the production of food materials since enzymes tend to lose their activity in the presence of the cross-linking agent and, what is more, the level of safety available with the reagent conventionally used in this reaction is inadequate.

In the support-binding method, loss of the enzyme activity is avoided by binding it to a support by an appropriate means such as covalent bonding. However, the specific types of enzyme applicable to this method are limited since the difficulty of binding is often encountered for particular combinations of an enzyme and a support. Use of a strong cross-linking agent such as glutaraldehyde to increase the bindability is not appropriate in the production of food materials from the viewpoint of safety, as stated above.

Combination methods are not appropriate for the production of food materials because of the toxicity of glutaraldehyde which is used as the conventional cross-linking agent.

Iridoids, which are used as the cross-linking agent in accordance with the process of the present invention, are known. This term refers to a group of compounds which are obtained from the fruit of tree gardenia. They react with compounds having primary amino groups and subsequently polymerize oxidatively to form blue pigments. Reference is made to Japanese Patent Publication No. 57-14781 and Japanese Patent Laid-Open No. 61-47167. This pigment is commonly used as a natural colorant for pigmenting food material and thus its safeness is generally accepted.

SUMMARY OF THE INVENTION

The present invention provides a method of producing an immobilized enzyme wherein the activity of the starting enzyme dose not suffer any significant decrease during the process of the immobilization onto a support.

The present invention further provides a method of producing an immobilized enzyme wherein use of any component that would be toxic to the human body can be avoided.

The present invention further provides a method of producing an immobilized enzyme wherein the enzyme activity can be kept stable even after repeated use.

The present invention further provides an immobilized enzyme which is as active as the free enzyme, is free from any toxic component, and yet remains stable even after repeated use.

DETAILED EXPLANATION OF THE INVENTION

Figure 1:
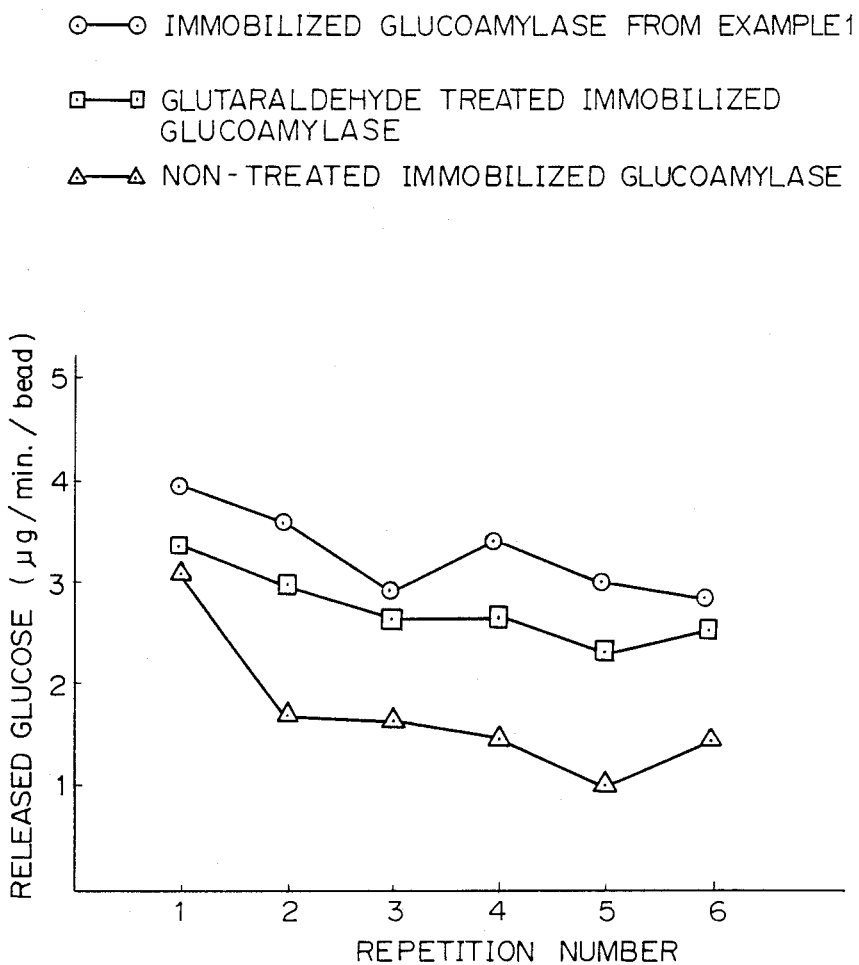
FIG. 1 represents a graph showing the influence of repeated use on enzyme activity when the immobilized glucoamylases of Example 1 and Comparative Example 1 were repeatedly used to digest starch.

It has been found that when an iridoid, e.g. genipin, is used as a cross-linking agent, it shows a remarkably strong ability to form cross-linkage among enzyme molecules or between said molecules and functional groups such as amino groups of a support having such a functional group, and yet it has little adverse effect on the enzyme activity. The present invention was accomplished on the basis of these findings.

Accordingly, the method of immobilizing an enzyme according to the present invention is characterized by the use of an iridoid as a new type of cross-linking agent in place of the conventional cross-linking agent typified by glutaraldehyde, the cross-linking agent being used for the formation of cross-linkage among the enzyme molecules or between said molecules and functional groups of a support in order that said enzyme will be immobilized.

Immobilization of an enzyme in accordance with the method of the invention can be conducted by any method involving cross-linkage formation which has been conventionally employed to prepare immobilized enzymes provided that the cross-linking agent is selected from among iridoids. For example, the immobilized enzyme of the invention can be produced by the cross-linking polymerization method. Thus the starting enzyme is brought into contact with a support, such as chitosan beads, as will be explained later, in an aqueous solution, thereby allowing adsorption of the enzyme on the support. The support which now carries the enzyme is next immersed in a solution containing an iridoid to facilitate the cross-linking polymerization of the enzyme molecules and the binding of the polymers on the support surface. The binding of the polymers on the support may be carried out by physical adsorption but it is desirable to use a support having a functional group such as amino group or the equivalent thereof in order to facilitate cross-linkage formation between the enzyme and the support, whereby an immobilized enzyme with stable activity can be obtained.

Alternatively, in order to prepare an immobilized enzyme of the invention by the combination method of cross-linking polymerization and gel-inclusion, the enzyme can, for example, be reacted with an iridoid in an aqueous solution to allow the enzyme to form cross-linking polymerization. The cross-linked enzyme polymers are then enclosed in a gel-inclusion agent (which will be explained hereinafter) such as an arginate to give the immobilized enzyme.

The method of the present invention may be employed to immobilize any enzyme since it enables efficient polymerization of enzymes by way of the cross-linking reaction and yet does not adversely affect their activities.

The types of iridoids employable in accordance with the present invention are not specifically restricted so long as they are capable of facilitating the cross-linking reaction. Preferably, however, they are selected from nontoxic aglycones of glycosides such as geniposide, gardenoside and geniposide acid. Genipin is most preferred.

As the support for immobilizing enzyme by use of cross-linking polymerization, chitosan beads, ion exchange resins, activated carbon and synthetic adsorption resins are exemplified, while the inclusion material employable in the combination method may be selected from natural polymers such as arginates, carrageenin, agar and agarose etc., or synthetic polymers such as polyacrylamides, polyacrylamide hydrazides and polyurethanes etc.

In order to produce the immobilized enzyme of the invention, the iridoid mediated cross-linking reaction among the enzyme molecules or between said molecules and the functional group of the support takes place in an aqueous solution while standing still or being stirred for a period of 2 to 70 hours at a pH of 4 to 10, preferably 6 to 8 and at a temperature of 5° to 50° C., more preferably at an ambient temperature. The amount of iridoid used for the crosslinkage formation is 0.001 to 0.1, preferably 0.005 to 0.05 parts per 1 part of the enzyme on the basis of the dry material.

The present invention will now be explained by way of non-limiting examples.

EXAMPLE 1

To a glucoamylase solution which contained 4.0 mg of the enzyme (40,000 units) in 40 ml of water, 1,000 particles of chitosan beads BCW-3013 (available from Fuji-Boseki Co., Ltd., Japan) were added and the mixture was gently stirred for 2 hours. Five milliliters of genipin solution in water (5%) was added thereto and the mixture was gently stirred for 18 hours. The chitosan beads were removed and then washed twice with distilled water (10 ml for each) to obtain glucoamylase immobilized chitosan beads. The enzyme activity of the beads was determined at 4,000 units/1,000 particles. One unit of the enzyme activity here is defined to mean a degree of activity that will release 1 $\mu$g of glucose in a minute at 37° C.

EXAMPLE 2

A protease preparation (7.5 mg: 0.18 units) (purchased from Sigma Chemical) originating from a microorganism of Streptomyces was dissolved in distilled water (15 ml). Protease immobilized chitosan beads were prepared from this solution in a similar way to that used in Example 1. The activity of the resulting beads was 0.023 units/1,000 particles. One unit of the enzyme activity here is defined to mean a degree of activity that will release 1 $\mu$g of tyrosine in a minute at 37° C.

EXAMPLE 3

A naringinase preparation (5 mg: 3.8 units) (purchased from Sigma Chemical) originating from a fungus of Aspergillus was dissolved in distilled water (15 ml). Naringinase immobilized chitosan beads were prepared from this solution in a similar way to that used in Example 1. The activity of the resulting beads was 2.0 units/1,000 particles. One unit of the enzyme activity here is defined to mean a degree of activity that will hydrolyze 1 $\mu$ mole of naringin in a minute at 37° C.

EXAMPLE 4

Sodium arginate (800 mg) was added to distilled water under gentle stirring. To this solution was added a cellulase preparation (500 mg: 150 units) (Cellulase TO available from Amino Pharmaceutical Co., Ltd., Japan) which was allowed to dissolve therein. Genipin (50 mg) was added thereto, the solution was stirred for 18 hours and the solution was then added dropwise to 1% calcium chloride in water (200 ml) under stirring, whereby a bead shaped gel was obtained. The gel beads were washed twice with a 0.1 M acetate buffer (200 ml), pH 4.5, containing 0.1% calcium chloride to give 32 ml of Cellulase TO immobilized beads. The resulting beads had an average diameter of 2 mm, average volume 6 $\mu$l and enzyme activity of 75 units/32 ml beads. One unit of the enzyme activity here is defined to mean a degree of activity that will hydrolyze 1 $\mu$ mole of geniposide in a minute at 37° C.

COMPARATIVE EXAMPLE 1

In a similar method to that used in Example 1, comparative immobilized chitosan beads which had not been subjected to the treatment with aqueous genipin solution (hereinafter referred to as "non-treated immobilized glucoamylase") and a further comparative immobilized chitosan beads which had been treated with 2.5% glutaraldehyde solution in water (5 ml) in place of the treatment with the aqueous genipin solution (hereinafter referred to as "glutaraldehyde treated immobilized glucoamylase") were obtained. The enzyme activities of the two comparative immobilized glucoamylase preparations were determined at the same value of 3,200 units/1,000 particles.

COMPARATIVE EXAMPLE 2

In a similar method to that employed in Example 2, comparative immobilized chitosan beads which had not been subjected to the treatment with aqueous genipin solution (hereinafter referred to as "non-treated immobilized protease") and a further comparative immobilized chitosan beads which had been treated with 2.5% glutaraldehyde solution in water (5 ml) in place of the treatment with the aqueous genipin solution (hereinafter referred to as "glutaraldehyde treated immobilized protease") were obtained. The enzyme activities of the two immobilized protease preparations were determined at the same value of 0.016 units/1,000 particles.

COMPARATIVE EXAMPLE 3

In a similar method to that used in Example 3, comparative immobilized chitosan beads which had not been subjected to the treatment with aqueous genipin solution (hereinafter referred to as "non-treated immobilized naringinase") and a further comparative immobilized chitosan beads which had been treated with 2.5% glutaraldehyde solution in water (5 ml) in place of the treatment with the aqueous genipin solution (hereinafter referred to as "glutaraldehyde treated immobilized naringinase") were obtained. The enzyme activity of the resulting non-treated immobilized naringinase was determined at the value of 0.4 units/1,000 particles and that of the glutaraldehyde treated immobilized naringinase was determined at the value of 2.1 units/1,000 particles.

COMPARATIVE EXAMPLE 4

In a similar method to that used in Example 4, a comparative immobilized calcium arginate beads which had not been subjected to the treatment with aqueous genipin solution (hereinafter referred to as "non-treated immobilized cellulase") and a further comparative immobilized calcium arginate beads which had been treated with 25% glutaraldehyde solution in water (0.4 ml) in place of the treatment with the aqueous genipin solution (hereinafter referred to as "glutaraldehyde treated immobilized cellulase") were obtained. The enzyme activity of the resulting non-treated immobilized cellulase was determined at the value of 25 units/32 ml beads and that of the glutaraldehyde treated immobilized cellulase was determined at the value of 35 units/32 ml beads.

EXAMPLE 5

One hundred particles each of the immobilized glucoamylase from Example 1, and the non-treated- and glutaraldehyde treated-immobilized glucoamylase from Comparative Example 1 were added separately to 0.6% soluble starch (9 ml) and the mixture was incubated under shaking at 40° C. for 30 minutes. The liquid in the container was then collected and replaced with the same volume of fresh soluble starch. This procedure was repeated 6 times and the reducing sugar in each of the collected samples of liquid was quantitated by Somogyi's method. The results are shown in FIG. 1 from which it is observed that the activity and stability of the immobilized enzyme in Example 1 were superior or at least equal to the immobilized enzyme produced by the glutaraldehyde treatment.

EXAMPLE 6

Figure 2:
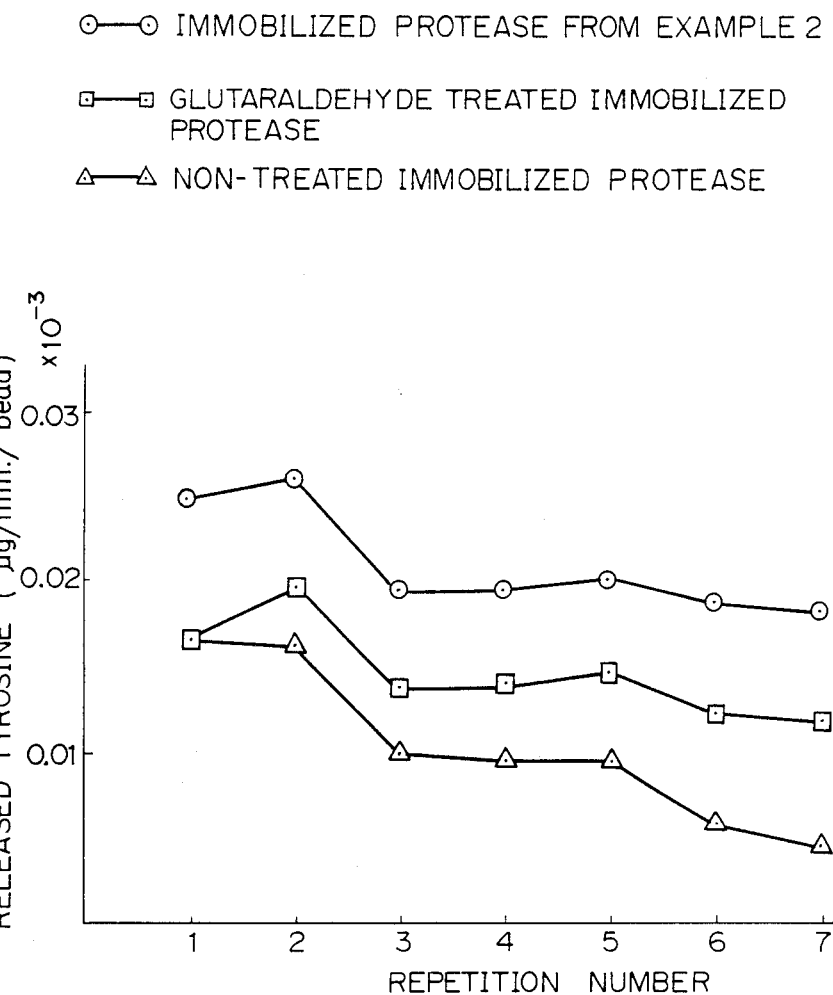
FIG. 2 represents a graph showing the influence of repeated use on enzyme activity when the immobilized proteases of Example 2 and Comparative Example 2 were repeatedly used to digest casein.

Five hundred particles each of the immobilized protease from Example 2, and the non-treated- and glutaraldehyde treated-immobilized protease from Comparative Example 2 were added separately to 1% casein solution in water (5 ml) and the mixture was incubated under shaking at 37° C. for 10 minutes. The liquid in the container was then collected and replaced with the same volume of fresh casein solution. This procedure was repeated 7 times. Trichloroacetic acid was then added to each of the collected samples of liquid to cause the undigested protein components in the liquid to precipitate. The phenol reagent was added to the supernatant to quantitate the digested non-precipitable product in the liquid by the absorbancy at 660 nm. The results given in FIG. 2 indicate that the immobilized protease of Example 2 was superior to those of Comparative Example 2 in terms of both activity and stability.

EXAMPLE 7

Figure 3:
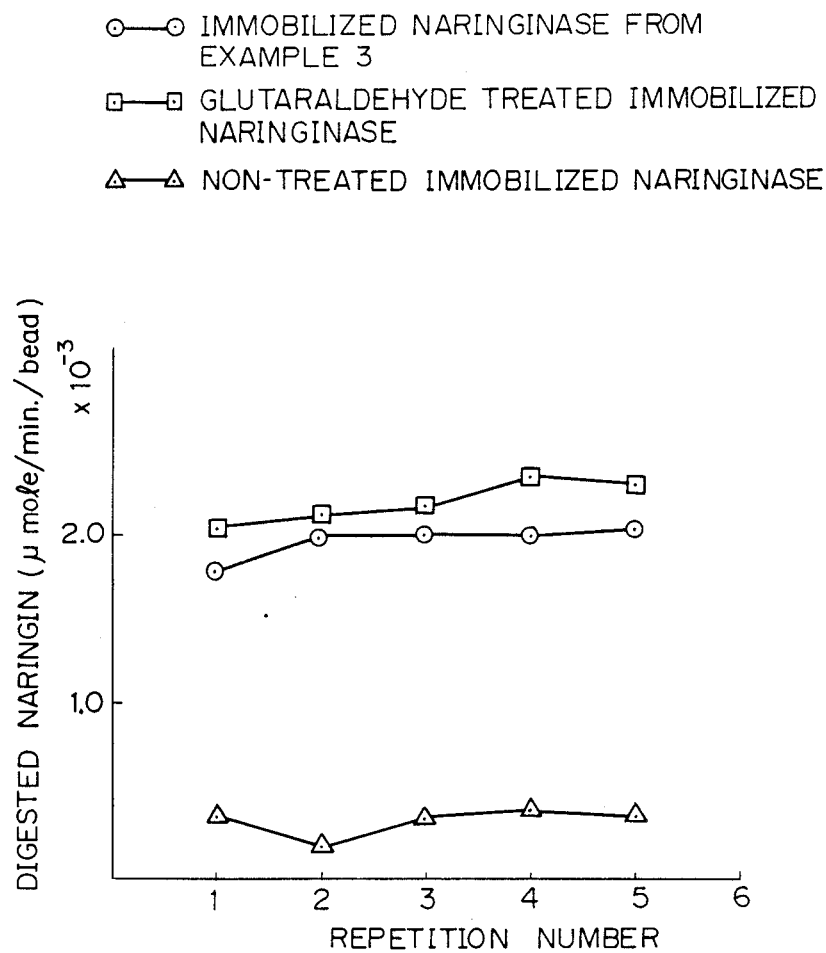
FIG. 3 represents a graph showing the influence of repeated use on enzyme activity when the immobilized naringinases of Example 3 and Comparative Example 3 were repeatedly used to digest naringin.

Forty particles each of the immobilized naringinase from Example 3, and the non-treated and glutaraldehyde treated-immobilized naringinase from Comparative Example 3 were added separately to 2 mM naringin solution in water (pH 5.0) and the mixture was incubated under shaking at 40° C. for 20 minutes. The liquid in the container was then collected and replaced with the same volume of fresh naringin solution. This procedure was repeated 5 time. The remaining naringin in each of the collected samples of liquid was then quantitated by high performance liquid chromatography (HPLC). The results shown in FIG. 3 reveal that the immobilized naringinase of Example 3 and the glutaraldehyde treated immobilized naringinase of Comparative Example 3 were substantially equal in terms of their activity and stability.

EXAMPLE 8

Figure 4:
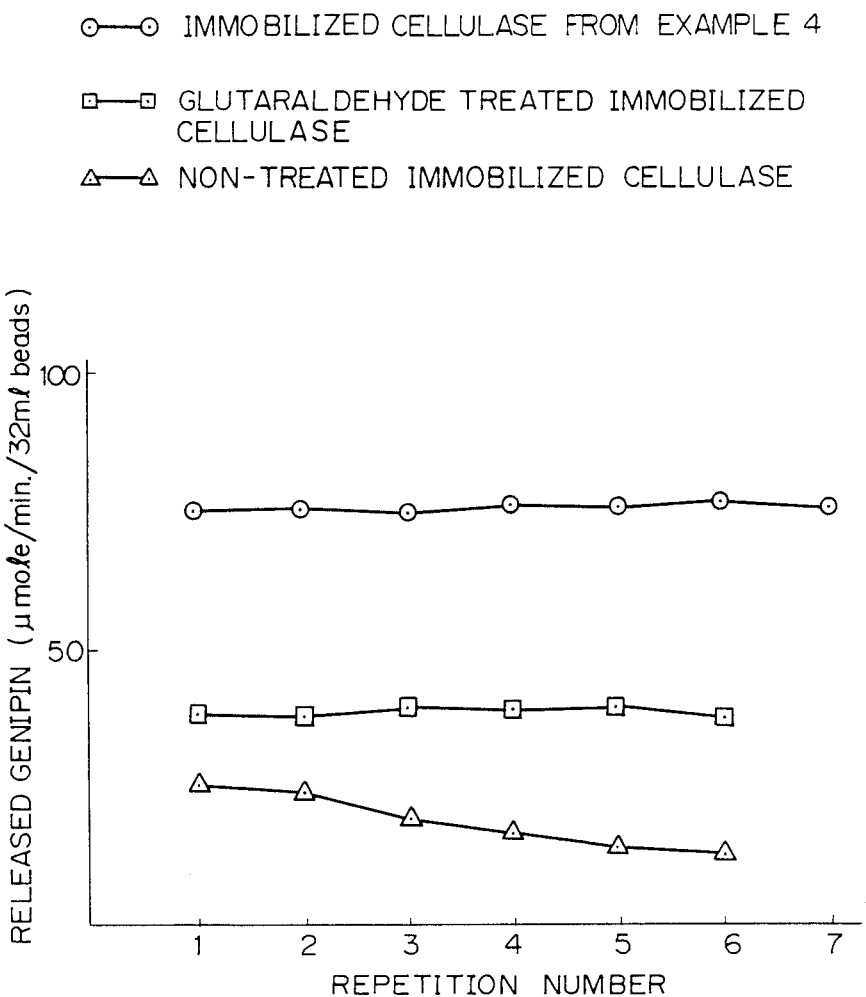
FIG. 4 represents a graph showing the influence of repeated use on enzyme activity when the immobilized cellulases of Example 4 and Comparative Example 4 were repeatedly used to digest geniposide.

One milliliter each of the immobilized cellulase from Example 4, and the non-treated and glutaraldehyde treated-immobilized cellulase from Comparative Example 4 were added separately to 130 mM geniposide solution in water (10 ml) and the mixture was incubated under gentle stirring at 40° C. for 16 hours. The liquid in the container was then collected and replaced with the same volume of fresh geniposide solution. This procedure was repeated 6 times. The genipin in each of the collected samples of liquid was quantitated by HPLC. From the results shown in FIG. 4, it can be seen that the immobilized cellulase of the invention experienced no decrease in activity even after being used 6 times.

What is claimed is:

1. A method for immobilizing an enzyme on a support comprising the steps of:
   (a) contacting an enzyme with a support in a solution containing an iridoid aglycone cross-linking agent to immobilize the enzyme on the support; and
   (b) collecting the immobilized enzyme resulting from step (a).

2. The method according to claim 1, wherein said cross-linking agent is an aglycone from an iridoid glycoside which is selected from the group consisting of geniposide, gardenoside and geniposide acid.

3. The method according to claim 1, wherein said contacting effects cross-linking polymerization among enzyme molecules.

4. The method according to claim 1, wherein said contacting effects cross-linking polymerization among enzyme molecules and cross-linking between enzyme molecules and functional groups of the support.

5. The method according to claim 1, wherein said cross-linking agent is genipin.

6. The immobilized enzyme obtained by the method of claim 1.

7. A method for immobilizing an enzyme in a gel comprising the steps of:
(a) contacting an enzyme with an iridoid aglycone cross-linking agent in a solution in order to effect cross-linking polymerization among enzyme molecules;
(b) enclosing the polymerized enzyme resulting from step (a) in a gel substance; and
(c) collecting the immobilized enzyme enclosed in the gel substance.

8. The method according to claim 7, wherein said cross-linking agent is an aglycone from an iridoid glycoside which is selected from the group consisting of geniposide, gardenoside and geniposide acid.

9. The immobilized enzyme obtained by the method of claim 7.

10. The method according to claim 7, wherein said cross-linking agent is genipin.

* * * * *